United States Patent
Simon et al.

[11] Patent Number: 6,016,440
[45] Date of Patent: Jan. 18, 2000

[54] DEVICE FOR INFRARED (IR) SPECTROSCOPIC INVESTIGATIONS OF INTERNAL SURFACES OF A BODY

[75] Inventors: Arno Simon, Karlsruhe; Wilfried Hartmann, Halle/Saale, both of Germany

[73] Assignee: Bruker Analytik GmbH, Rheinstetten, Germany

[21] Appl. No.: 08/889,159

[22] Filed: Jul. 7, 1997

[30] Foreign Application Priority Data

Jul. 29, 1996 [DE] Germany .......................... 196 30 627

[51] Int. Cl.⁷ ...................................................... A61B 6/00
[52] U.S. Cl. .......................... 600/473; 600/160; 600/182
[58] Field of Search ...................................... 600/473, 478, 600/110, 146, 164, 174, 181, 474, 475, 310, 160, 182, 176, 177, 170, 171

[56] References Cited

U.S. PATENT DOCUMENTS

| | | | |
|---|---|---|---|
| 4,272,156 | 6/1981 | Ishibashi et al. | 350/96.26 |
| 4,273,111 | 6/1981 | Tsukaya | 600/473 |
| 4,349,032 | 9/1982 | Koyata | 600/437 |
| 4,403,273 | 9/1983 | Kimihiko | 362/32 |
| 4,493,313 | 1/1985 | Nagasaki . | |
| 4,494,549 | 1/1985 | Namba et al. | 600/437 |
| 4,562,831 | 1/1986 | Murakoshi et al. | 358/98 |
| 4,674,515 | 6/1987 | Andou et al. | 600/437 |
| 4,736,734 | 4/1988 | Matsuura et al. | 350/96.26 |
| 4,759,347 | 7/1988 | Ando | 358/98 |
| 4,782,818 | 11/1988 | Mori | 128/6 |
| 4,982,725 | 1/1991 | Hibino et al. | 600/146 |
| 5,054,491 | 10/1991 | Saito et al. | 600/466 |
| 5,058,568 | 10/1991 | Irion et al. | 128/4 |
| 5,255,087 | 10/1993 | Nakamura et al. | 358/98 |
| 5,304,173 | 4/1994 | Kittrell et al. | 606/15 |
| 5,318,024 | 6/1994 | Kittrell . | |
| 5,325,847 | 7/1994 | Matsuno | 600/160 |
| 5,398,685 | 3/1995 | Wilk et al. | 600/407 |
| 5,434,669 | 7/1995 | Tabata et al. | 356/345 |
| 5,445,157 | 8/1995 | Adachi et al. | 600/473 |
| 5,491,551 | 2/1996 | Mattson . | |
| 5,573,493 | 11/1996 | Sauer et al. | 600/121 |
| 5,596,992 | 1/1997 | Haaland et al. | 600/473 |
| 5,667,474 | 9/1997 | Nishimura | 600/109 |
| 5,800,341 | 9/1998 | McKenna et al. | 600/109 |

FOREIGN PATENT DOCUMENTS

| | | |
|---|---|---|
| 1920775 | 5/1965 | Germany . |
| 2746614 | 4/1979 | Germany . |
| 3202080 | 10/1982 | Germany . |
| 34 31 022 C2 | 3/1985 | Germany . |
| 3537904 | 4/1986 | Germany . |
| 3817915 | 11/1989 | Germany . |
| 2283091 | 4/1995 | United Kingdom . |
| 9511624 | 5/1995 | WIPO . |

*Primary Examiner*—Brian L. Casler
*Attorney, Agent, or Firm*—Paul Vincent

[57] ABSTRACT

A device for infrared (IR) spectroscopic investigation of internal surfaces of a body, for example of blood vessels, comprising an endoscope (10) with light guide means to illuminate the surfaces is characterized in that at the distal end of the light guide means there is arranged a detector (12) for detecting IR light scattered from the illuminated surface and transforming it into electric signals. For otherwise identical conditions, compared to comparable known devices, the device according to the invention offers a higher signal strength and thereby the possibility to shorten the measuring time for equal signal quality.

18 Claims, 2 Drawing Sheets

Fig. 1
Fig. 2
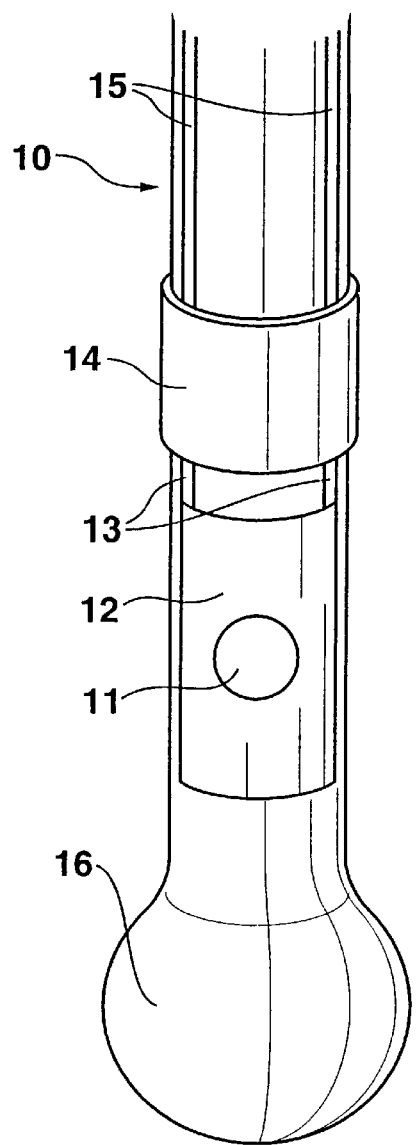
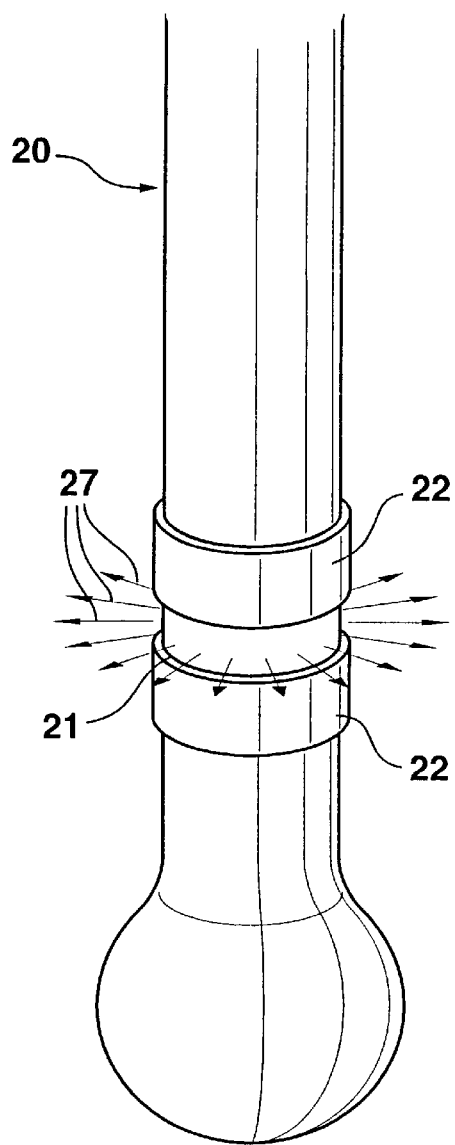

DEVICE FOR INFRARED (IR) SPECTROSCOPIC INVESTIGATIONS OF INTERNAL SURFACES OF A BODY

BACKGROUND OF THE INVENTION

The invention concerns a device for infrared (IR) spectroscopic investigation of internal surfaces of a body, for example of blood vessels with an IR spectrometer and with an endoscope with light guide means to illuminate the surfaces.

Such a device is known from WO 95/11624.

In endoscopes of such devices, scattered light is guided from internal surfaces of a body, mostly from blood vessels or internal body cavities via light guides to an external outside detector. Generally, glass fiber bundles are used as light guides. The light intensity of the detected scattered light and therefore the signal strength is thereby essentially proportional to the product of glass fiber cross sections which guide the light along the endoscope to the exposure, and the cross section of those glass fibers which collect the scattered light and guide it to the outside detector.

These prior art devices have therefore the disadvantage that for a given total cross section of the glass fibers only a fraction of the cross section can be used for illumination of the internal surfaces since the remaining glass fibers serve for guiding the collected light to the outside.

Apart from this, the collecting surface, i.e. the possible range of observation, is limited by the cross section of the collecting glass fibers and therefore relatively small in comparison to the total coating surface of the endoscope. The collecting fibers, suitable for spectroscopy (e.g. quartz) transfer the collected light only within a relatively narrow acceptance angle (generally a cone with ±10°), leading to an additional strong spatial limitation of the light acceptance of scattered light by the endoscope.

From DE 27 46 614 A1, an endoscope is known with light guide means to illuminate investigated surfaces. The illuminating light for the endoscope comes from a cold light source or from illuminating diodes located at the distal end, but from a spectrometer. DE 27 46 614 A1 is only concerned with imaging, not with spectroscopy.

In U.S. Pat. No. 4,403,273, a rod-shaped reflection unit for the illumination system of an endoscope is presented which allows a particularly large field of view of more than 100°.

In DE-GM 19 20 775, at the distal end of an endoscope a fiber light guide is bent by about 90°, polished at its flat end and covered by an opal glass plate. Insertable optics enable sidewise directed observation.

In U.S. Pat. No. 5,058,568, it is suggested to use the protective metal cover weave or other elements of a flexible endoscope for electric connections, which can lead e.g. to a video chip at the distal end.

U.S. Pat. No. 4,674,515 describes a rotatable ultrasound head of an endoscope.

U.S. Pat. No. 4,782,818, finally, discloses an endoscope to illuminate internal body surfaces with visible light for therapeutic reasons.

It is therefore the purpose of the present invention to present an device of the kind described above which comprises, for otherwise equal conditions, an increased signal strength and thereby the possibility to reduce the measuring time for equal signal quality.

SUMMARY OF THE INVENTION

According to the invention, this aim is achieved in a way, equally surprisingly simple and effective, in that at the proximal end IR light is directed from the IR spectrometer into the light guide means and that at the distal end of the light guide means there is arranged a detector for detecting IR light scattered from the illuminated surface and transforming it into electric signals.

By this detector arrangement no "return guide" for the collected scattered light is needed any more in the light guide means, so that the total light guiding cross section of the light guide means can fully be used to illuminate the surfaces under investigation. The accepting surface of the endoscope of the invention is merely limited by the detector design but not by the cross section of "return" glass fibers. The angular limitation of the acceptable scattered light due to the relatively small acceptance angle of glass fibers is also not relevant any more. In this way, for an equally large outer circumference of the endoscope, a considerably higher light yield can be achieved and thereby a considerably higher signal strength, so that for a comparable quality of the spectra a considerably shorter measuring time is required compared to conventional endoscopes.

An embodiment of the device according to the invention is particularly preferred where the detector comprises a sensitive detector surface which is larger than the cross section of the light exit surface at the distal end of the light guide means. In this way, also the diffusively scattered light of the investigated surface can be collected and thereby the light and signal yield of the device according to the invention can be considerably improved over conventional ones.

The IR spectrometer is preferably an FTIR spectrometer with an interferometer whose interfering light beam is coupled into the light guide means at their proximal end and which spectrometer converts the electric detector signals into an interferogram and by means of Fourier transformation into an IR spectrum.

Since a detector at the distal end is used, the IR light has to pass the spectrometer prior to entering the light guide means. Fourier spectrometer have a much better light yield compared to monochromators. However, in embodiments, the IR spectrometer may also be a dispersive system, i.e. a grating or prism spectrometer with entrance and exit slits.

The light guide means may comprise one or more commercially available glass fiber bundles.

In a preferred improvement of these embodiments, means to deflect the light by about 90° are provided at the distal end of the light guide means. In this way, an investigation range can be illuminated extending crosswise to the longitudinal endoscope axis as is typically the case with blood vessels.

The deflection may be effected by a tilted mirror or by a prism fitted onto the glass fiber bundle.

In an improvement that can be manufactured particularly easily and therefore cheaply, the means to deflect the light are formed by a prismatic cut of the glass fiber ends at about 45°. The light deflection is based upon total reflection or a reflective coating of the tilted surfaces.

In embodiments, the space between the fibers of the glass fiber bundle is filled with a material that, in the spectral range of interest, comprises a refractive index such that the refractive index difference between fiber and material is small enough for transmission of the IR light incident at nearly right angle and emerging from other fibers due to total reflection at their cut ends.

In this way the light bundles emerging e.g. from the central fiber can pass the peripheral fibers largely without reflection losses.

In order to ensure guidance of the IR light inside the fibers, their surfaces can be reflectively coated outside the distal region where the light leaves the fibers.

Preferably, the space between the fibers of the glass fiber bundle are at least in the region where the light leaves the fibers filled with a material which, in the spectral range of interest, comprises a refractive index such that the refractive index difference between fiber and material is large enough to guide the IR light inside the fibers but small enough for transmission of the IR light incident at nearly right angle and emerging from other fibers due to total reflection at their cut ends.

The problem that the outer fibers are in the way of the light deflected out of the inner fibers can be avoided in an elegant way by the following preparation procedure: After the prismatic (or cone shaped) cut and polishing, the longest fibers of the fiber bundle are pulled back in such a way that a staircase shaped arrangement is formed in the region of the light deflection in such a way that the light emerging out of a particular fiber deflected at an angel of about 90° is not blocked by other fibers. The fibers that during the cutting and polishing had still been the longest ones become the shortest ones at the distal end and vice versa.

However, apart from this, any other optical means to deflect light can also be used.

In a particularly preferred embodiment of the device according to the invention, the sensitive detector surface is placed directly on a coating surface of the light guide means. In this way, the detector practically requires no extra room and the endoscope of the device according to the invention can be constructed in a particularly compact manner.

In an advantageous improvement of this embodiment, provision is made that at the distal end of the light guide means the deflected light emerges within a limited angular range essentially in one direction on one side of the light guide means and that the sensitive detector surface is arranged on that side of the coating surface of the light guide means. In this way, a defined location of the internal surface surrounding the endoscope can be investigated selectively, whereby the arrangement of the sensitive detector surface on the same side where the light emerges leads to a particularly high yield of scattered light in relation to the detector surface.

A particularly advantageous improvement of this embodiment is characterized in that the deflected light emerges from a, preferably circular, mask on the side of the light guide means and that the sensitive detector surface is arranged on this side of the coating surface around the mask aperture. In particular, by using the mask, a collimation of the illuminating light and thereby a collimation onto a particularly small investigation surface precisely to the point can be achieved. Since the sensitive detector surface immediately surrounds the mask aperture, the detected light yield is further optimized.

Alternatively, in another advantageous embodiment of the device according to the invention, the deflected light may emerge out of an annular mask encircling the coating surface of the light guide means and the sensitive detector surface is arranged annularly about the coating surface of the light guide means, preferably on both sides of the annular mask aperture. In this way, for fixed endoscope, a complete annular surface range around the endoscope can be investigated simultaneously.

In a particularly preferred embodiment, the sensitive detector surface consists of a, preferably 1 to 10 μm thick, lead sulfide (PbS) layer which is particularly suited to accept infrared light.

In a further embodiment of the device according to the invention, the detector comprises a commercially photo resistor available at low cost.

The endoscope of the device according to the invention is particularly compact in embodiments where conducting strips are placed onto the coating surface of the light guide means, preferably by vapor deposition, to conduct the electric signals produced in the detector.

In an alternative embodiment, thin wires are provided to conduct the electric signals produced in the detector, preferably inside a channel in the center of the light guide means. This embodiment, too, does not enlarge the outer circumference of the endoscope.

In a particularly preferred improvement of this embodiment, the distal end of the light guide means can be mechanically manipulated by means of the thin wires. In this way, the signal wires serve a further function which had otherwise to be taken over by other components, so that, by this modification, the endoscope of the device according to the invention can again be designed in a particularly compact manner.

In a further, alternative embodiment, commercially available metal coated glass fibers, in particular gold coated glass fibers, are provided to conduct the electric signals generated in the detector.

Particularly preferred is also an embodiment of the device according to the invention, where the light guide means comprises at its distal end immediately after the detector a digitizing unit to digitize the electric signals generated by the detector. In this way, the signal received by the detector can be transported over far distances in digitized form even for small signal strengths.

A further advantageous embodiment is characterized in that a rotatable component is arranged at the distal end of the light guide means which can be manipulated from the other end of the light guide means and which deflects the light emerging out of the light guide means in a direction corresponding to the respective rotation angle of the rotatable component. In this way, the azimuthal resolution of the endoscope of the device according to the invention can alternatively be limited to a small angular range or be extended to an annular range around the entire surrounding surface, for example a blood vessel wall.

The same effect can be achieved by an alternative embodiment, where the endoscope of the device according to the invention is rotatable about its longitudinal axis. In comparison to the embodiment described above, there is, however, the disadvantage that the endoscope must be rotated over its entire length, which can lead to complications at locations with narrow passages, in particular during medical investigations at the point of insertion of the endoscope into the human body.

Also advantageous is an embodiment where the detector can be translated along the longitudinal axis of the endoscope. In this way, for fixed endoscope, measurements reflecting a longitudinal dependence become nevertheless possible.

In a particularly preferred embodiment, the light guide means comprises at its distal end an ultrasound head, preferably rotatable about the longitudinal endoscope axis. In this way, critical locations, for example narrow vessel passages, can be pre-localized by ultrasound measurements. Subsequently, specific infrared measurements can be performed, for example to identify the kind of tissue or depositions.

In a particularly compact improvement of this embodiment, the signal leads for the ultrasound head coincide with the electric leads which conduct also the electric signals from the detector receiving IR light. Separation of the two signal kinds may for example be effected by using disjunct voltage, current or frequency ranges and possibly by transfer of the IR detector signal in digital form and of the ultrasound signal in analogue form.

Further advantages of the invention result from the description and the drawing. The above mentioned features and those to be further described below in accordance with the invention can be utilized individually or collectively in arbitrary combination.

The embodiments shown and described are not to be considered as exhaustive enumeration, rather have exemplary character only for the description of the invention.

The invention is represented in the drawing and is further explained in connection with embodiments.

BRIEF DESCRIPTION OF THE DRAWING

FIG. 1 shows a schematic three-dimensional representation of an endoscope of a device according to the invention with a circular mask;

FIG. 2 shows an endoscope of a device according to the invention with a circumferential annular mask;

DESCRIPTION OF THE PREFERRED EMBODIMENTS

Figure 3:
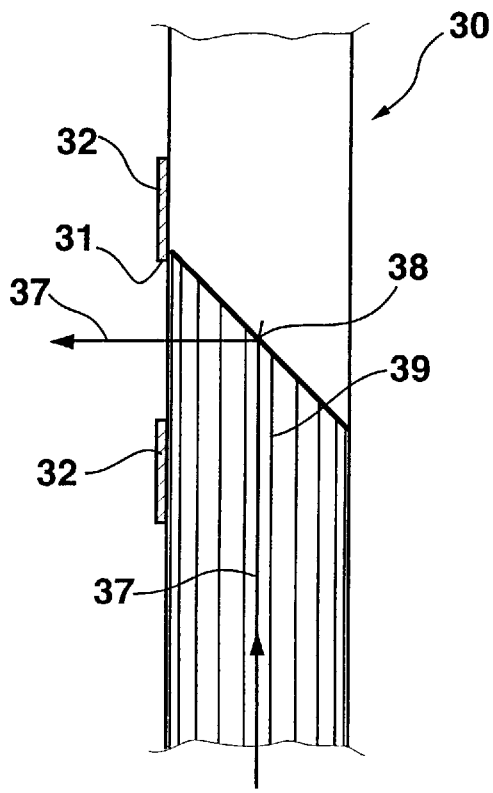
FIG. 3 shows a detail of a schematic longitudinal cross section across an endoscope of a device according to the invention with sidewise deflection of the illuminating light in a direction as in FIG. 1.

The three dimensional representation in FIG. 1 shows the distal end of the light guide means of an endoscope 10, serving to infrared (IR) spectroscopically investigate internal surfaces of a body, as for example internal walls of a blood vessel, stomach, intestines or the like. Not visible in FIG. 1, endoscope 10 internally contains light guide means, generally comprising glass fiber bundles. At the distal end of endoscope 10, the light, guided along the light guide means, is deflected by about 90° and emerges from a mask 11, being circular in the embodiment shown, in a direction at right angles to the endoscope 10 axis in the form of a light beam in a limited angular range and illuminates a corresponding spot of the surface under investigation. The light, back-scattered from there, is collected by means of a detector 12 at least to large extent and transformed into electric signals, which are transferred via leads 13 to a digitizing unit 14. From this, the digitized signals are conducted to the outside for further processing, via leads 15, which, in the embodiment shown, are vapor deposited onto the coating surface of the endoscope.

At the lowest end of endoscope 10, an ultrasound head 16 is schematically represented, with which advance ultrasound measurements of the investigation area can be performed prior to the IR spectroscopic investigations. In this way, for example critical locations as e.g. narrow vessel passages or depositions can at first be pre-localized by the ultrasound measurements and subsequently a specific tissue identification or generally of substances at the investigation area can be performed. Preferably, ultrasound head 16 will be rotatable about the longitudinal endoscope 10 axis. In order to keep the endoscope 10 as compact a possible regarding its outer dimensions, the same electric leads 13, 15 can be used for both, the electric measuring signals from ultrasound head 16 as well as for the electric measuring signals from detector 12, whereby both electric signal kinds may for example be separated by using different voltage, current or frequency ranges.

Detector 12 collecting IR light scattered by the illuminated surface, and converting it into electric signals, is flat in the presented embodiment, whereby the sensitive detector surface is attached to a coating surface of endoscope 10. The sensitive detector surface can for example consist of a, preferably 1 to 10 $\mu$m thick, PbS layer. In particular, detector 12 can comprise a photo resistor.

In the embodiment shown in FIG. 1, the sensitive detector surface of detector 12 is arranged around mask aperture 11. Since back-scattered light from the object surface can only be collected on the side of the mask aperture, in this case the sensitive detector 12 surface is limited approximately to a half cylinder around the mask aperture 11. The sensitive detector surface is nevertheless still considerably larger than the light exit area at the distal end of the light guide means of endoscope 10, so that at least most of the IR light scattered at the examination surface can be collected. Moreover, the detector surface according to the invention does not lead to the usual angular limitations of glass fibers for the observed light due to the finite acceptance angle of glass fibers.

In FIG. 2 a further embodiment is shown, where instead of a circular mask 11 the endoscope 20 comprises a circumferential annular mask 21, from which the light 27, deflected inside the endoscope 20 by about 90°, emerges to all sides. The sensitive detector 22 surface consists in this case of two circumferential annular strips arranged at both sides of annular mask aperture 21. With such an arrangement, an entire annular surface range around the endoscope 20 can be investigated simultaneously.

The above mentioned light deflection at the illuminated end of light guide means of about 90° can for example be effected by a fitted prism or a prismatic cut of the light guide ends. In FIG. 3 an axial section at the distal end of an endoscope 30 of a device according to the invention is represented in a longitudinal cross section. IR light from a spectrometer 1 enters the light guide means. A central IR light beam 37 runs inside a glass fiber bundle 39 and impinges on a prism surface 38 at the distal end of the glass fiber bundle 39 and is deflected in the shown figure towards the left side. It exits sidewise out of the endoscope 30, through a mask aperture 31, formed by an e.g. circular hole in the sensitive surface of a detector 32. In combination with other light beams from neighboring fibers of glass fiber bundle 39 a collimated light beam is thereby formed being angularly limited, which illuminates a correspondingly limited investigation surface located sidewise from the endoscope 30. Insofar FIG. 3 represents the possible "interior" of an endoscope 10 according to FIG. 1.

Figure 4:
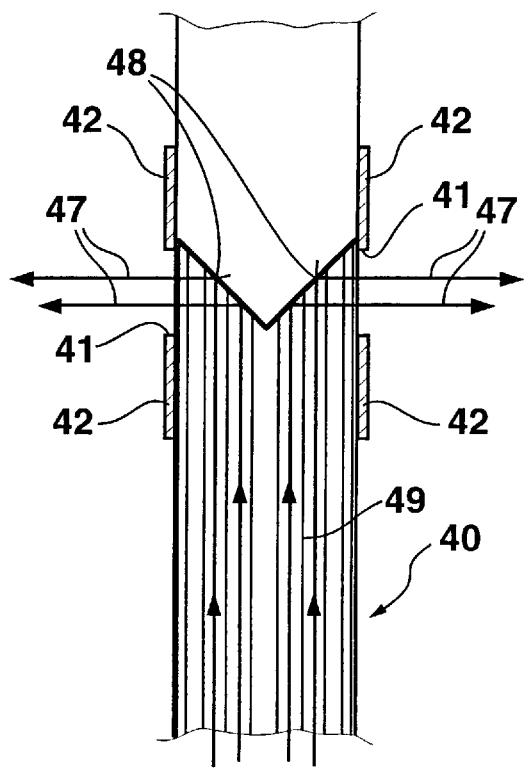
FIG. 4 shows a detail of a schematic longitudinal cross section across an endoscope of a device according to the invention with annular light deflection as in FIG. 2.

FIG. 4 shows also in a longitudinal cross section a detail of an endoscope 40, exhibiting similar annular circumferential illumination characteristics as endoscope 20 of FIG. 2. In a glass fiber bundle 49 there are schematically represented light beams 47 originating in spectrometer 1, impinging at the end of the light guide means onto a cone shaped tilted surface 48 of a correspondingly shaped deflecting component attached to the fiber bundle end, where they experience a sidewise total reflection by 90°. The tilted surface 48 may also be reflectively coated. The light beams 47 then exit through an annular mask aperture 41 in all directions perpendicular to the endoscope 40. Annular mask 41 is formed by the sensitive surfaces of a detector 42 which are arranged as strips above and below the aperture range around the coating surface of endoscope 40.

Figure 5A:
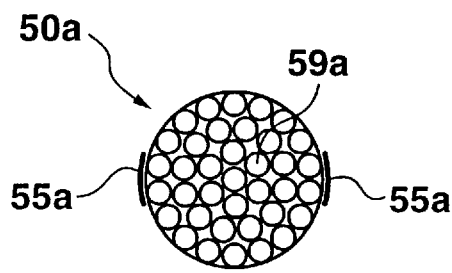
FIG. 5a shows a schematic cross section across an endoscope of a device according to the invention with vapor deposited conducting strips.
Figure 5B:
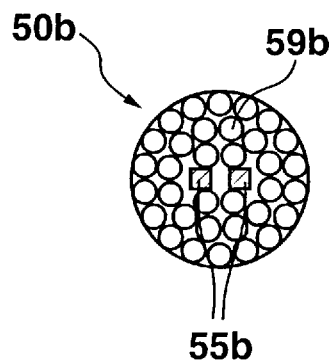
FIG. 5b shows a schematic cross section across an endoscope of a device according to the invention with conducting wires running in a channel.

FIGS. 5a and 5b, each show a schematic cross section across an endoscope of a device according to the invention. Tightly packed glass fiber bundles 59a, 59b can be recognized which serve to guide the illuminating light.

The endoscope represented in FIG. 5a comprises conducting strips 55a which are vapor deposited sidewise onto the coating surface of endoscope 50a to conduct the measuring signals generated by the detector.

In contrast thereto, endoscope 50b of FIG. 5b comprises two wires 55b in an internal channel between the glass fibers 59b, which wires 55b are represented with a rectangular cross section for better distinction which serve also to conduct the detector signals and which, in practice, would exhibit a round, considerably smaller cross section. In addition, the wires 55b, if correspondingly arranged, can take over mechanical tasks, e.g. effect a rotation of an ultrasound head at the distal end of endoscope 50b.

The endoscope of the device according to the invention can be designed such that at the distal end of the light guide means a rotatable component is arranged which can be manipulated and which deflects the light emerging from the light guide means in a direction corresponding to the respective rotation angle of the rotatable component. By rotating this head piece of the endoscope, measuring of a sequential series of spectra across the entire circumference of the surrounding surface which has to be investigated becomes possible.

In addition, a longitudinal shift of the optical system inside the endoscope can also be possible, whereby also a translatoric scan of the surface regions under investigation and from this a large scale investigation is possible.

In particular if already data are generated in digital form at the distal end of the endoscope, the detector and/or a corresponding AD converter could also transmit these date in a wireless manner without electric leads. Detector and/or transmitter could be equipped with a microbattery, i.e. electric leads could be omitted completely.

We claim:

1. Device for an infrared (IR) spectroscopic investigation of internal surfaces of a body, e.g. of blood vessels, comprising an IR spectrometer (1) and an endoscope (10, 20; 30; 40; 50a; 50b) with light guide means inside the endoscope to illuminate the internal surfaces, with means to direct IR light from the IR spectrometer (1) at a proximal end of the light guide means into the light guide means and at a distal end of the light guide means a detector (12; 22; 32; 42) for detecting IR light scattered from the illuminated internal surfaces and generating corresponding electric signals, wherein the IR spectrometer is a Fourier spectrometer with an interferometer which converts the electric signals into an interferogram and by Fourier transformation into an IR spectrum and the detector (12; 22; 32; 42) comprises a sensitive detector surface, which is larger than a light exit area at the distal end of the light guide means, wherein the light guide means comprise a glass fiber bundle (39; 49; 59a; 59b) and at the distal end of the light guide means (38; 48) means are provided to deflect the light by about 90°, wherein the sensitive detector surface is attached to a coating surface of the light guide means.

2. Device according to claim 1, characterized in that the means to deflect the light include a prismatic cut (38) of the glass fiber ends (39).

3. Device according to claim 2, characterized in that in a distal region of the light guide means where the IR light leaves the fibers, a space between the fibers of the glass fiber bundle is filled with a material that, in an IR spectral range of interest, comprises a refractive index such that the refractive index difference between fiber and material is small enough for transmission of the IR light emerging from other fibers due to reflection at their cut ends.

4. Device according to claim 3, characterized in that outside the distal region of the light guide means where the light leaves the fibers, the fiber surfaces are reflectively coated.

5. Device according to claim 2, characterized in that a space between the fibers of the glass fiber bundle are at least in the region where the light leaves the fibers filled with a material which, in an IR spectral range of interest, comprises a refractive index such that the refractive index difference between fiber and material is large enough to guide the IR light inside the fibers but small enough for transmission of the IR light emerging from other fibers due to reflection at their cut ends.

6. Device according to claim 2, characterized in that after the prismatic cut the fibers of the glass fiber bundle are longitudinally shifted with respect to one another in such a way that a staircase shaped arrangement is formed at the distal end of the light guide means such that the light emerging out of a particular fiber deflected at an angle of about 90° is not blocked by other fibers.

7. Device according to claim 1, characterized in that at the distal end of the light guide means the deflected light (37) emerges within a limited angular range essentially in one direction on one side of the light guide means and that the sensitive detector surface is arranged on that side of the coating surface of the light guide means.

8. Device according to claim 7, characterized in that the deflected light (37) emerges from a mask aperture (11, 31) on a side of the light guide means and that the sensitive detector surface is arranged on this side of the coating surface around the mask aperture (11; 31).

9. Device according to claim 1, characterized in that, the deflected light (27, 47) emerges out of an annular mask aperture (21; 41) encircling the coating surface of the light guide means and the sensitive detector surface is arranged annularly about the coating surface of the light guide means, preferably on both sides of the annular mask aperture (21; 41).

10. Device according to claim 1, characterized in that the sensitive detector surface consists of a 1 to 10 $\mu$m thick PbS layer.

11. Device according to, claim 1, characterized in that thin wires (55b) are provided to conduct the electric signals generated in the detector (22), preferably inside a channel in the center of the light guide means.

12. Device according to claim 1, characterized in that the light guide means comprises at its distal end an ultrasound head (16) rotatable about the longitudinal endoscope axis.

13. Device according to claim 12, characterized in that signal leads for the ultrasound head (16) coincide with electric leads (15) which conduct the electric signals from the detector (12).

14. The device of claim 1, wherein said light deflection means comprises a prism.

15. Device for an infrared (IR) spectroscopic investigation of internal surface of a body, e.g. of blood vessels, comprising an IR spectrometer (1) and an endoscope (10, 20; 30; 40; 50*a*; 50*b*) with light guide means inside the endoscope to illuminate the internal surfaces, with means to direct IR light from the IR spectrometer (1) at a proximal end of the light guide means into the light guide means and at a distal end of the light guide means a detector (12; 22; 32; 42) for detecting IR light scattered from the illuminated internal surfaces and generating corresponding electric signals, wherein conducting strips (13; 15; 55*a*) are placed onto a coating surface of the light guide means, preferably by vapor deposition, to conduct the electric signals generated in the detector (12).

16. Device for an infrared (IR) spectroscopic investigation of internal surfaces of a body, e.g. of blood vessels, comprising an IR spectrometer (1) and an endoscope (10, 20; 30; 40; 50*a*; 50*b*) with light guide means inside the endoscope to illuminate the internal surfaces, with means to direct IR light from the IR spectrometer (1) at a proximal end of the light guide means into the light guide means and at a distal end of the light guide means a detector (12; 22; 32; 42) for detecting IR light scattered from the illuminated internal surfaces and generating corresponding electric signals, wherein thin wires (55*b*) are provided to conduct the electric signals generated in the detector (22), preferably inside a channel in the center of the light guide means, and the distal end of the light guide means can be mechanically manipulated by means of the thin wires (55*b*).

17. Device for an infrared (IR) spectroscopic investigation of internal surfaces of a body, e.g. of blood vessels, comprising an IR spectrometer (1) and an endoscope (10, 20; 30; 40; 50*a*; 50*b*) with light guide means inside the endoscope to illuminate the internal surfaces, with means to direct IR light from the IR spectrometer (1) at a proximal end of the light guide means into the light guide means and at a distal end of the light guide means a detector (12; 22; 32; 42) for detecting IR light scattered from the illuminated internal surfaces and generating corresponding electric signals, wherein metal coated glass fibers are provided to conduct the electric signals generated in the detector (22).

18. Device for an infrared (IR) spectroscopic investigation of internal surfaces of a body, e.g. of blood vessels, comprising an IR spectrometer (1) and an endoscope (10, 20; 30; 40; 50*a*; 50*b*) with light guide means inside the endoscope to illuminate the internal surfaces, with means to direct IR light from the IR spectrometer (1) at a proximal end of the light guide means into the light guide means and at a distal end of the light guide means a detector (12; 22; 32; 42) for detecting IR light scattered from the illuminated internal surfaces and generating corresponding electric signals, wherein a rotatable component is arranged at the distal end of the light guide means which can be manipulated from the proximal end of the light guide means and which deflects the IR light emerging out of the light guide means in a direction corresponding to a respective rotation angle of the rotatable component.

* * * * *